US012773491B2

(12) United States Patent
Wine et al.

(10) Patent No.: US 12,773,491 B2
(45) Date of Patent: Oct. 27, 2026

(54) DRIP CHAMBER WITH NEEDLE VALVE

(71) Applicant: CareFusion 303, Inc., San Diego, CA (US)

(72) Inventors: Jason Wine, Placentia, CA (US); Eugene Mason, La Habra Heights, CA (US)

(73) Assignee: CAREFUSION 303, INC., San Diego, CA (US)

( * ) Notice: Subject to any disclaimer, the term of this patent is extended or adjusted under 35 U.S.C. 154(b) by 953 days.

(21) Appl. No.: 16/655,094

(22) Filed: Oct. 16, 2019

(65) Prior Publication Data

US 2021/0113764 A1 Apr. 22, 2021

(51) Int. Cl.
*A61M 5/14* (2006.01)
*A61M 5/168* (2006.01)

(52) U.S. Cl.
CPC ...... *A61M 5/1411* (2013.01); *A61M 5/16813* (2013.01); *A61M 5/16881* (2013.01)

(58) Field of Classification Search
CPC ...... A61M 2039/226; A61M 2039/229; A61M 2039/2473; A61M 2039/2486; A61M 39/22; A61M 5/1411; A61M 5/168; A61M 5/16804; A61M 5/16813; A61M 5/16877; A61M 5/16881; A61M 5/162; A61M 5/1689; A61M 5/40
See application file for complete search history.

(56) References Cited

U.S. PATENT DOCUMENTS 3,761,052 A 9/1973 Tobbe et al.
3,963,024 A * 6/1976 Goldowsky ............. A61M 5/40 604/254
4,431,021 A 2/1984 Scaramucci
4,789,000 A * 12/1988 Aslanian ........... A61M 5/16881 604/32
5,730,730 A * 3/1998 Darling, Jr. ............. A61M 5/40 604/254
6,279,594 B1 8/2001 Beitzel
(Continued)

FOREIGN PATENT DOCUMENTS

CN 2612383 Y 4/2004
CN 102772842 B 4/2014
(Continued)

OTHER PUBLICATIONS

International Preliminary Report on Patentability for Application No. PCT/US2020/055625, dated Apr. 28, 2022, 8 pages.
(Continued)

*Primary Examiner* — Shefali D Patel
(74) *Attorney, Agent, or Firm* — MASCHOFF BRENNAN

(57) ABSTRACT

A valve body is disclosed to control fluid flow through a chamber body defining a chamber volume, and the valve body comprises a chamber body coupling, a valve inlet, a valve outlet, and a needle valve assembly. The chamber body coupling receives the chamber body. The valve inlet or the valve outlet is configured to be in fluid communication with the chamber volume. The needle valve assembly comprises a fixed needle valve surface and a movable needle valve surface, wherein the movable needle valve surface is axially movable relative to the fixed needle valve surface to control a flow rate between the valve inlet and the valve outlet.

16 Claims, 8 Drawing Sheets

(56) References Cited

U.S. PATENT DOCUMENTS

| | | | |
|---|---|---|---|
| 9,867,730 | B2 | 1/2018 | Jackson |
| 2011/0125103 | A1 | 5/2011 | Rondeau |

FOREIGN PATENT DOCUMENTS

| | | | |
|---|---|---|---|
| CN | 105377326 | A | 3/2016 |
| CN | 106714858 | A | 5/2017 |
| GB | 1554629 | | 10/1979 |
| GB | 2059776 | A | 4/1981 |
| GB | 2089944 | | 6/1982 |
| JP | S4891625 | A | 11/1973 |
| JP | S56100064 | A | 8/1981 |
| JP | S57139343 | U | 8/1982 |
| JP | S61124639 | U | 8/1986 |
| JP | 2013512044 | A | 4/2013 |
| WO | WO-8600682 | A1 | 1/1986 |
| WO | WO-2011066443 | A1 | 6/2011 |

OTHER PUBLICATIONS

International Search Report and Written Opinion for Application No. PCT/US2020/055625, dated Feb. 5, 2021, 13 pages.
Chinese Office Action for Application No. 202080087618.X, dated Dec. 28, 2023, 22 pages including translation.
Japanese Office Action for Application No. 2022-522854, dated Jul. 3, 2024, 9 pages including translation.
Chinese Office Action for Application No. 202080087618.X, dated Jul. 2, 2024, 16 pages including translation.
Chinese Office Action for Application No. 202080087618.X, dated Oct. 23, 2024, 22 pages including translation.
Indian Office Action for Application No. 202217023935, dated Dec. 10, 2024, 6 pages.
Japanese Office Action for Application No. 2022-522854, dated Nov. 6, 2024, 9 pages including translation.
Alternate English language translation of previously cited Japanese Publication No. JPS57139343U, retrieved by the European Patent Office on Feb. 10, 2025, 3 pages.
Chinese Decision of Rejection for Application No. 202080087618.X, dated Mar. 19, 2025, 14 pages including translation.
European Office Action for Application No. 20801101.5, dated Feb. 13, 2025, 5 pages.
Japanese Decision Declining Amendment for Application No. 2022-522854, dated Mar. 7, 2025, 6 pages including machine translation.
Japanese Decision of Rejection for Application No. 2022522854, dated Mar. 7, 2025, 3 pages including machine translation.
Australian Office Action for Application No. 2020367791, dated Mar. 31, 2025, 4 pages.
Mexican Office Action for Application No. MX/a/004511, dated May 27, 2025, 9 pages including English language Memo.
Mexican Office Action for Application No. MX/a/2022/004511, dated Oct. 30, 2025, 11 pages including English language memo.
Australian Office Action for Application No. 2020367791, dated Mar. 4, 2026, 5 pages.
Australian Notice of Acceptance for Application No. 2020367791, dated Apr. 9, 2026, 3 pages.
Australian Office Action for Application No. 2020367791, dated Jan. 27, 2026, 4 pages.
European Office Action for Application No. 20801101.5, dated Dec. 9, 2025, 6 pages.
Canadian Office Action for Application No. 3,154,414, dated Jun. 18, 2026, 4 pages.
Mexican Office Action for Application No. MX/a/2022/004511, dated Apr. 16, 2026, 16 pages including machine translation.

* cited by examiner

DRIP CHAMBER WITH NEEDLE VALVE

FIELD OF THE INVENTION

The present disclosure generally relates to flow control devices, and, in particular, to flow control devices for tubing.

BACKGROUND

Medical treatments often include the infusion of a medical fluid (e.g., a saline solution or a liquid medication) to patients using an intravenous (IV) catheter that is connected through an arrangement of flexible tubing and fittings, commonly referred to as an "IV set," to a source of fluid, for example, an IV bag. During operation, the flow rate of the medical fluid can be changed with roller clamps.

SUMMARY

In some applications, roller clamps may not provide precise and reliable control of the flow rate of the medical fluid.

The disclosed subject matter relates to valve bodies. In certain embodiments, a valve body is disclosed to control fluid flow through a drip chamber defining a chamber volume and comprises a chamber body coupling, a valve inlet, a valve outlet, and a needle valve assembly. The chamber body coupling receives the drip chamber. The valve inlet or the valve outlet is configured to be in fluid communication with the chamber volume. The needle valve assembly comprises a fixed needle valve surface; and a movable needle valve surface, wherein the movable needle valve surface is axially movable relative to the fixed needle valve surface to control a flow rate between the valve inlet and the valve outlet.

In certain embodiments, a drip chamber is disclosed that comprises a chamber body defining a chamber volume and a valve body. The valve body includes a chamber body coupling, a valve inlet, a valve outlet, and a needle valve assembly. The chamber body coupling receives the drip chamber. The valve inlet or the valve outlet is configured to be in fluid communication with the chamber volume. The needle valve assembly comprises a fixed needle valve surface; and a movable needle valve surface, wherein the movable needle valve surface is axially movable relative to the fixed needle valve surface to control a flow rate between the valve inlet and the valve outlet.

In certain embodiments, a method to control fluid flow through a drip chamber is disclosed and comprises introducing fluid flow to a valve body in fluid communication with the drip chamber; moving a movable needle valve surface relative to a fixed needle valve surface; and directing fluid flow between the movable needle valve surface and the fixed needle valve surface to control fluid flow out of the valve body.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

The disclosed valve body incorporates a needle valve assembly to control the flow rate of a medical fluid. A movable needle valve surface can move relative to a fixed needle valve surface to adjust the flow rate. By moving the movable needle valve surface, the flow rate can be reliably and precisely controlled.

The detailed description set forth below is intended as a description of various configurations of the subject technology and is not intended to represent the only configurations in which the subject technology may be practiced. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology. Like components are labeled with identical element numbers for ease of understanding. Reference numbers may have letter suffixes appended to indicate separate instances of a common element while being referred to generically by the same number without a suffix letter.

While the following description is directed to the control of medical fluid during the administration of medical fluid using the disclosed valve body, it is to be understood that this description is only an example of usage and does not limit the scope of the claims. Various aspects of the disclosed valve body may be used in any application where it is desirable to control the flow of fluid.

The disclosed valve body overcomes several challenges discovered with respect to certain conventional clamps. One challenge with certain conventional clamps is that certain conventional clamps may not provide precise control of the flow rate. Further, certain conventional clamps may drift over time and may not maintain a desired flow rate. Because imprecise and/or unreliable delivery of medical fluid can compromise treatment, the use of conventional clamps is desirable.

Therefore, in accordance with the present disclosure, it is advantageous to provide a valve body as described herein that allows for precise and reliable flow control. The disclosed valve body provides a needle valve assembly that allows for precise and reliable flow control.

An example of a valve body that allows for precise and reliable flow control is now described.

Figure 1:
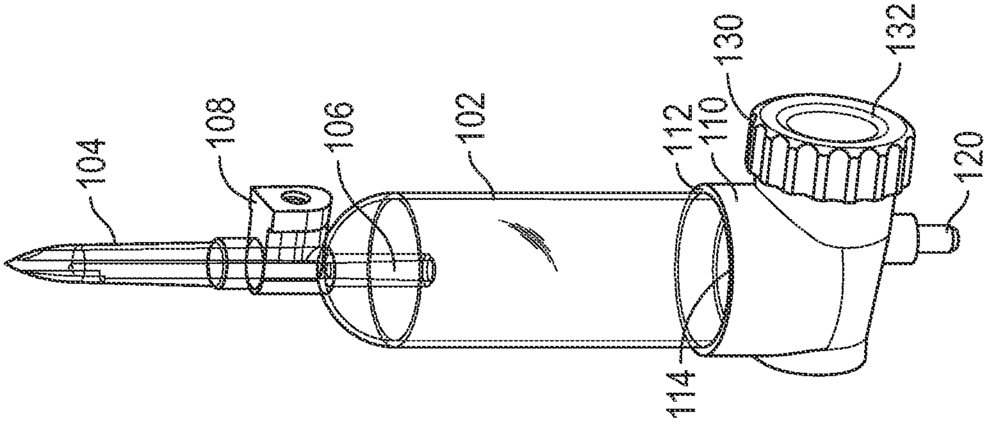
FIG. 1 is a perspective view of a drip chamber, in accordance with various aspects of the present disclosure.

FIG. 1 is a perspective view of a drip chamber 100, in accordance with various aspects of the present disclosure. In the depicted example, the drip chamber 100 provides a visual indicator of the flow rate of a medical fluid therethrough. Advantageously, clinicians can monitor and adjust the flow rate of the medical fluid based on the visual indicator provided by the drip chamber 100.

During operation, medical fluid can drip or otherwise flow through the chamber volume defined by the chamber body 102. As illustrated, medical fluid can enter the chamber body 102 through an inlet tube 106 defined in the chamber body 102. Fluid flow can exit the chamber body 102 through an outlet 120. As fluid passes through the chamber body 102, a clinician can utilize the drip chamber 100 as a visual indicator to observe the dripping or flow of medical fluid therethrough. As can be appreciated the chamber body 102 can be transparent or semi-transparent.

In some embodiments, the chamber body 102 can include an air vent 108 to equalize pressure differentials between the chamber volume and the environment during operation. In some embodiments, the chamber body 102 can be formed from a resilient material to allow the chamber body 102 to be squeezed or compressed to draw in medical fluid for priming of an IV system.

Optionally, the chamber body 102 can include a spike 104 to pierce membranes, such as an IV container membrane. In some embodiments, the inlet tube 106 can be formed through a spike 104 extending from the chamber body 102.

Figure 2:
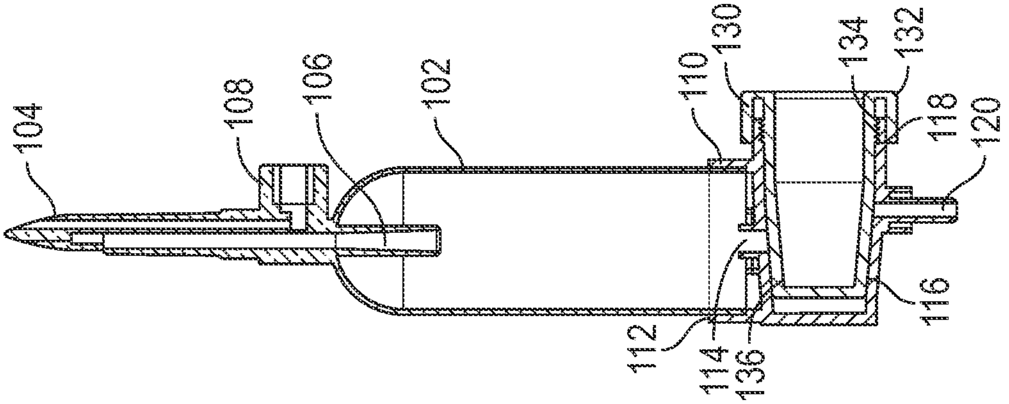
FIG. 2 is a cross-sectional view of the drip chamber of FIG. 1, in accordance with various aspects of the present disclosure.
Figure 3:
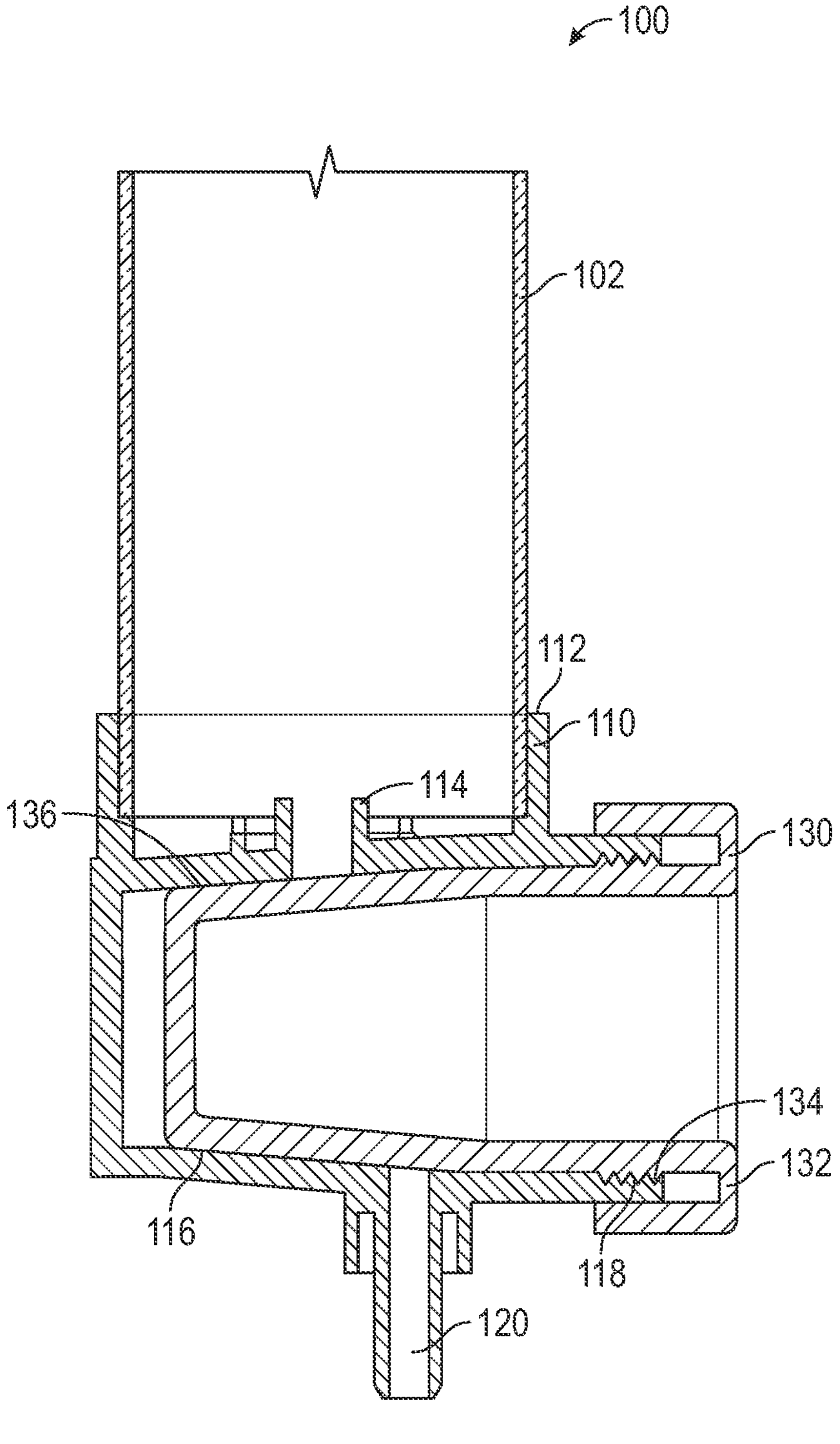
FIG. 3 is a partial cross-sectional view of the drip chamber of FIG. 1, in accordance with various aspects of the present disclosure.

FIG. 2 is a cross-sectional view of the drip chamber 100 of FIG. 1, in accordance with various aspects of the present disclosure. FIG. 3 is a partial cross-sectional view of the drip chamber 100 of FIG. 1, in accordance with various aspects of the present disclosure. With reference to FIGS. 1-3, the drip chamber 100 can also control the flow rate of the medical fluid passing therethrough. As described herein, the drip chamber 100 can utilize a needle valve assembly to precisely and reliably control the flow rate of the medical fluid.

In the depicted example, the valve body 110 of the drip chamber 100 is coupled to the chamber body 102 at a receiver or chamber body coupling 112. As illustrated, the valve body 110 is coupled to a lower end of the chamber body 102, permitting fluid flow from the chamber volume of the chamber body 102 to enter the valve body 110. As can be appreciated, the valve body 110 can be arranged in various configurations relative to the chamber body 102, for example as an inlet to the chamber body 102 or as an outlet to the chamber body 102.

In some embodiments, medical fluid from the chamber body 102 enters the valve body 110 at a valve inlet 114. Advantageously, the valve body 110 and the needle valve assembly therein controls the flow of fluid from the valve inlet 114 to the valve outlet 120.

In the depicted example, the needle valve assembly is formed by a fixed needle valve surface and a moveable needle valve surface. During operation, the movable needle valve surface can be moved relative to the fixed needle valve surface to adjust the cross-sectional area of the flow path between the valve inlet 114 and the valve outlet 120 to control the flow rate of the fluid therethrough. Therefore, during operation, the movable needle valve surface can be spaced apart from the fixed needle valve surface to provide an increased flow rate or the movable needle valve surface can be moved closer to the fixed needle valve surface to decrease the flow rate through the valve body 110. In some embodiments, the needle valve surfaces can be nested conical or frustoconical surfaces.

For example, the needle valve assembly can be formed between the valve body 110 and a knob assembly 130. Therefore, during operation, the valve body 110 and the knob assembly 130 can control the flow between the valve inlet 114 and the valve outlet 120. In the illustrated embodiment, the valve body 110 can define a fixed needle valve surface 116. The fixed needle valve surface 116 can receive the movable needle valve surface 136 of the knob assembly 130. By axially moving the knob assembly 130, the cross-sectional area of the flow path defined between the fixed needle valve surface 116 and the movable needle valve surface 136 can be adjusted to control the flow rate between the valve inlet 114 and the valve outlet 120. Accordingly, during operation, fluid flow from the chamber body 102 can enter the valve inlet 114, flow through the flow path defined between the fixed needle valve surface 116 and the movable needle valve surface 136 and exit the drip chamber 100 through the valve outlet 120.

As can be appreciated, the knob assembly 130 can be moved relative to the valve body 110 to adjust the flow rate between the valve inlet 114 and the valve outlet 120. In some embodiments, the knob assembly 130 can be in threaded engagement with the valve body 110 to allow for fine adjustment of the flow rate for the drip chamber 100. Therefore, by rotating the knob 132, the movable needle valve surface 136 of the knob assembly 130 can move relative to the fixed needle valve surface 116 of the valve body 110. In some embodiments, a threaded portion 134 of the knob assembly 130 can be in threaded engagement with a threaded portion 118 of the valve body 110.

In some embodiments, the knob assembly 130 can be axially actuated, by releasing or overcoming the threaded engagement between the knob assembly 130 and the valve body 110 to allow for coarse or rapid adjustment of the flow rate for the drip chamber 100.

Figure 4:
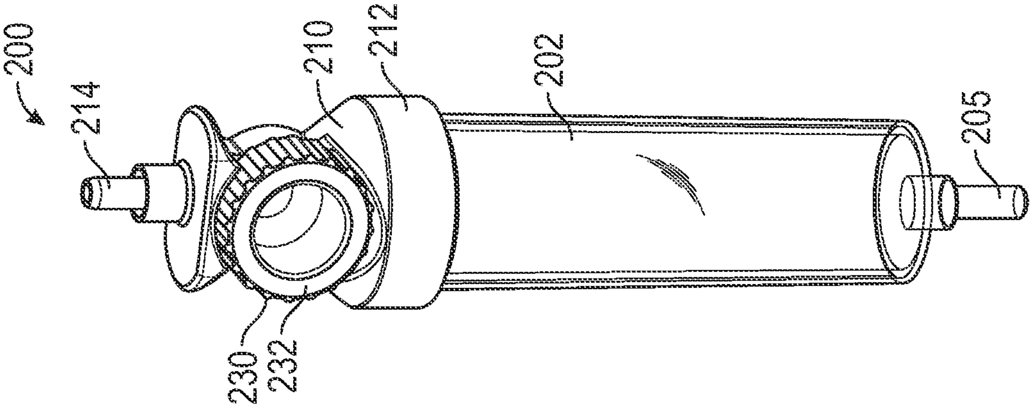
FIG. 4 is a perspective view of a drip chamber, in accordance with various aspects of the present disclosure.

FIG. 4 is a perspective view of a drip chamber 200, in accordance with various aspects of the present disclosure. As can be appreciated, the drip chamber 200 may include elements that are similar to drip chamber 100. Therefore, similar elements may be referred to by similar reference numerals. In the depicted example, the valve body 210 can be disposed at an upper end of the chamber body 202. Therefore, medical fluid can enter the chamber body 202 through the valve body 210 and can exit the chamber body 202 through a chamber outlet 205. As can be appreciated, the valve body 210 can control the flow rate of medical fluid through the chamber body 202.

Figure 5:
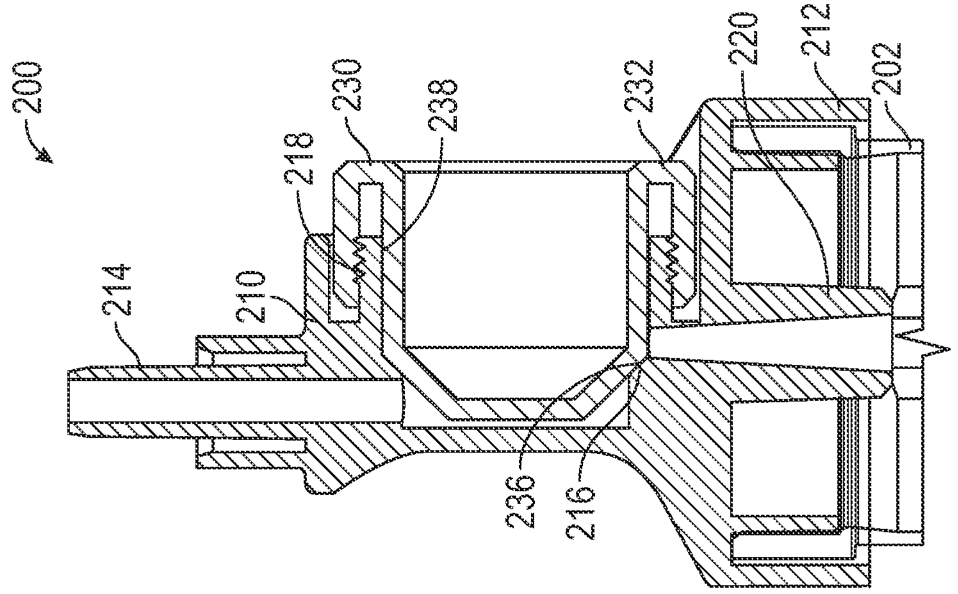
FIG. 5 is a partial cross-sectional view of the drip chamber of FIG. 4, in accordance with various aspects of the present disclosure.

FIG. 5 is a partial cross-sectional view of the drip chamber 200 of FIG. 4, in accordance with various aspects of the present disclosure. With reference to FIGS. 4 and 5, the valve body 210 is coupled to the upper portion of the chamber body 202 at the receiver or chamber body coupling 212. As can be appreciated, medical fluid enters the valve body 210 through the valve inlet 214 and exits into the chamber body 202 through the valve outlet 220.

Figure 6:
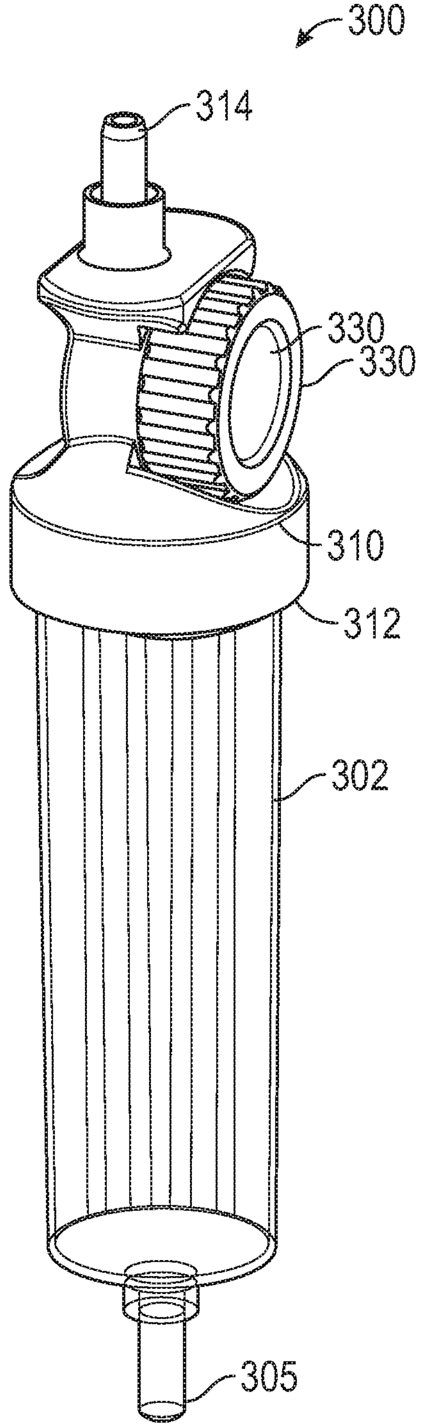
FIG. 6 is a perspective view of a drip chamber, in accordance with various aspects of the present disclosure.

FIG. 6 is a perspective view of a drip chamber 300, in accordance with various aspects of the present disclosure. As can be appreciated, the drip chamber 300 may include elements that are similar to drip chamber 200. Therefore, similar elements may be referred to by similar reference numerals. In some embodiments, the chamber body 302 can be reinforced with a plurality of ribs.

Figure 8:
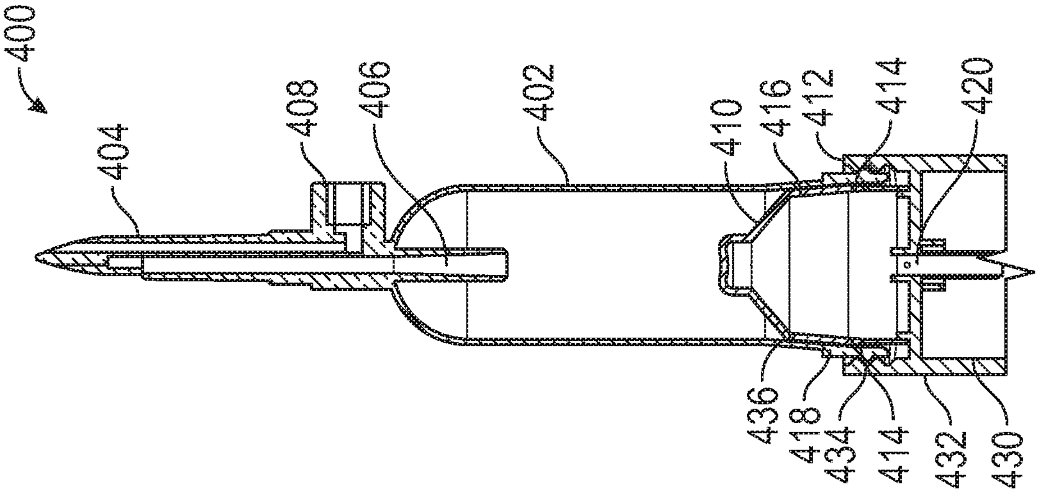
FIG. 8 is a cross-sectional view of the drip chamber of FIG. 7, in accordance with various aspects of the present disclosure.
Figure 7:
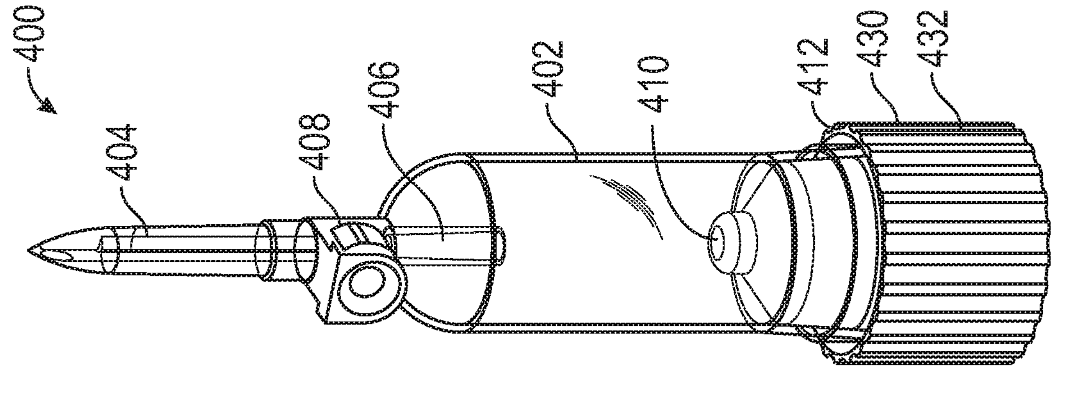
FIG. 7 is a perspective view of a drip chamber, in accordance with various aspects of the present disclosure.
Figure 9:
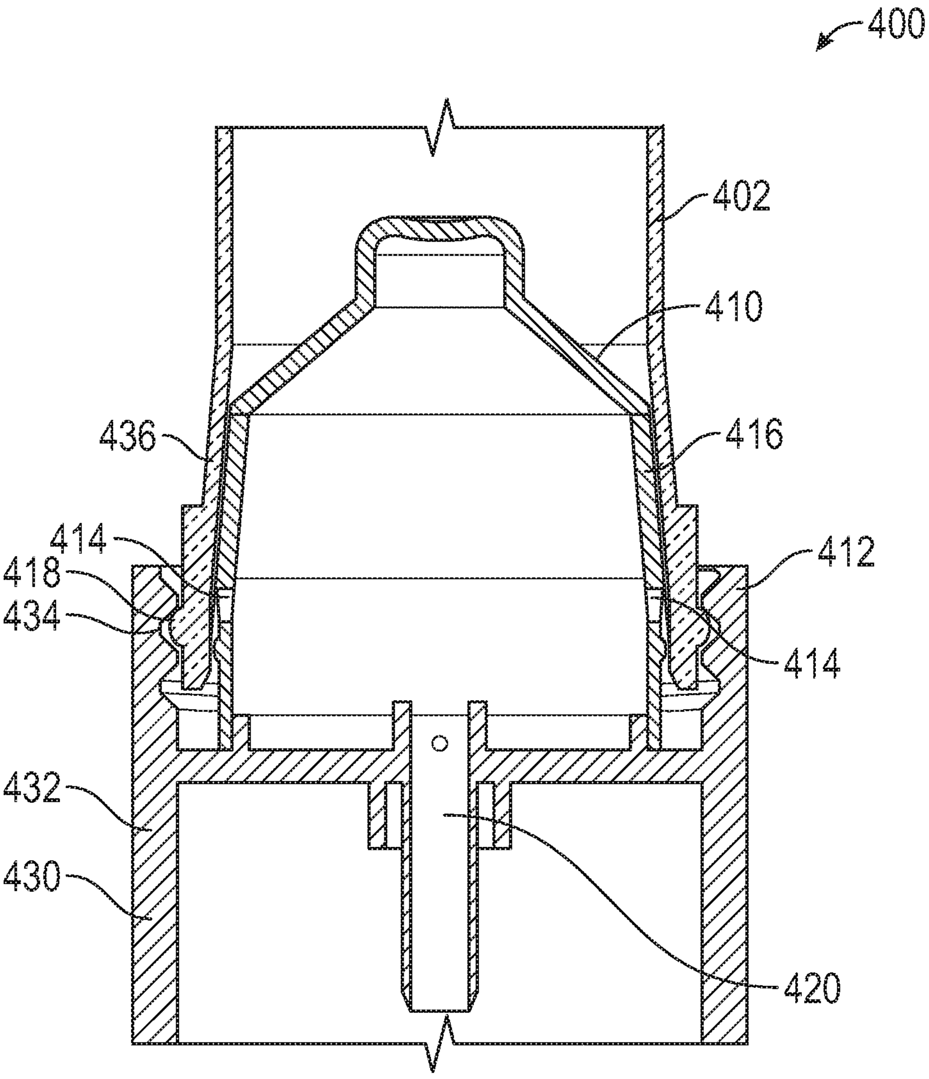
FIG. 9 is a partial cross-sectional view of the drip chamber of FIG. 7, in accordance with various aspects of the present disclosure.

FIG. 7 is a perspective view of a drip chamber 400, in accordance with various aspects of the present disclosure. FIG. 8 is a cross-sectional view of the drip chamber 400 of FIG. 7, in accordance with various aspects of the present disclosure. FIG. 9 is a partial cross-sectional view of the drip chamber 400 of FIG. 7, in accordance with various aspects of the present disclosure.

With reference to FIGS. 7-9, the drip chamber 400 may include elements that are similar to drip chamber 100. Therefore, similar elements may be referred to by similar reference numerals. In the depicted example, the drip chamber 400 can include a knob assembly 432 that is axially aligned with the chamber body 402. In some applications, the axially aligned knob assembly 432 may provide for various tubing configurations.

In the depicted example, the valve body 410 and the knob assembly 430 are coupled to the chamber body 402. In some embodiments, the knob assembly 430 is coupled to the chamber body 402 at a receiver or chamber body coupling 412 defined within the knob assembly 430. As illustrated, the valve body 410 and the knob assembly 430 can be coupled to a lower end of the chamber body 402, permitting fluid flow from the chamber body 402 to enter the valve body 410.

In the depicted example, the needle valve assembly defined between the valve body 410 and the chamber body 402 controls the flow of fluid from the chamber volume of the chamber body 402 into the valve inlets 414 and in turn, through the valve outlet 420.

In the depicted example, the needle valve assembly can be formed between the chamber body 402 and the valve body 410 to control the flow between the chamber volume and the valve inlet 414. In the illustrated embodiment, the valve body 410 can define a fixed needle valve surface 416. The fixed needle valve surface 416 can receive the movable needle valve surface 436 of the chamber body 402. By axially moving chamber body 402 relative to the valve body 410, the cross-sectional area of the flow path defined between the fixed needle valve surface 416 and the movable needle valve surface 436 can be adjusted to control the flow rate between the chamber volume and the valve inlet 114. Accordingly, during operation, fluid flow from the chamber body 402 flow through the flow path defined between the fixed needle valve surface 416 and the movable needle valve surface 436, enter the valve inlets 414, and exit the drip chamber 400 through the valve outlet 420.

As can be appreciated, the chamber body 402 can be moved relative to the valve body 410 to adjust the flow rate between the chamber volume and the valve inlet 414. In some embodiments, the knob assembly 430 is in threaded engagement with the chamber body 402 to allow for fine adjustment of the axial position of the chamber body 402 relative to the valve body 410 and therefore control the flow rate for the drip chamber 400. Therefore, by rotating the knob 432, the movable needle valve surface 436 of the chamber body 402 can move relative to the fixed needle valve surface 416 of the valve body 410. In some embodiments, a threaded portion 434 of the knob assembly 430 can be in threaded engagement with a threaded portion 418 of the chamber body 402.

Figure 11:
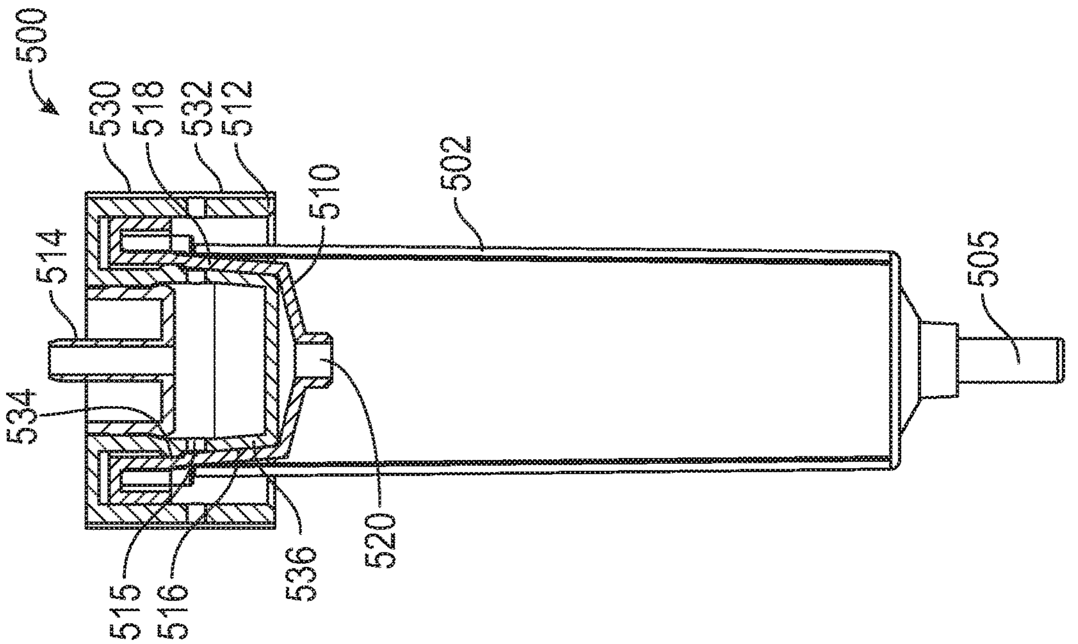
FIG. 11 is a cross-sectional view of the drip chamber of FIG. 10, in accordance with various aspects of the present disclosure.
Figure 10:
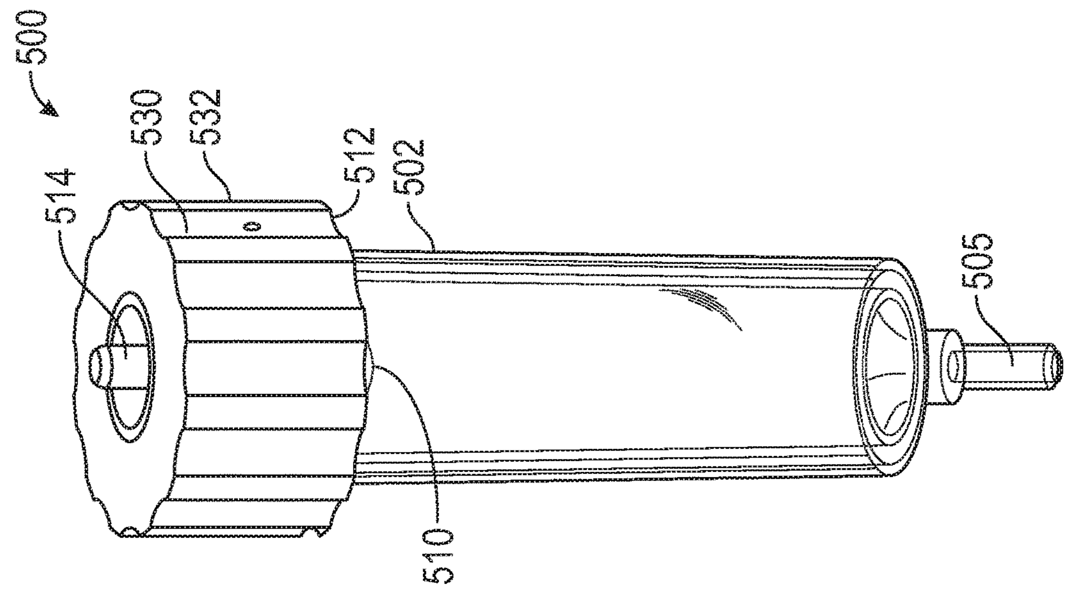
FIG. 10 is a perspective view of a drip chamber, in accordance with various aspects of the present disclosure.
Figure 12:
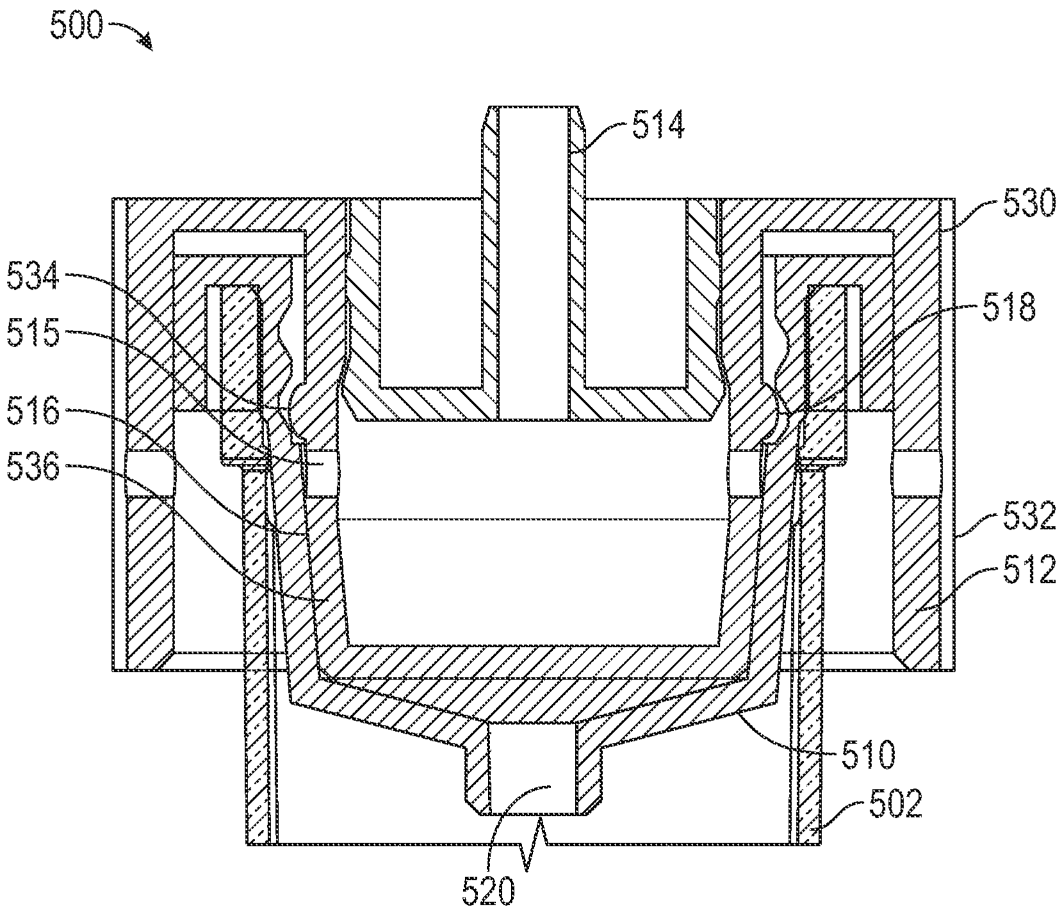
FIG. 12 is a partial cross-sectional view of the drip chamber of FIG. 10, in accordance with various aspects of the present disclosure.

FIG. 10 is a perspective view of a drip chamber 500, in accordance with various aspects of the present disclosure. FIG. 11 is a cross-sectional view of the drip chamber 500 of FIG. 10, in accordance with various aspects of the present disclosure. FIG. 12 is a partial cross-sectional view of the drip chamber 500 of FIG. 10, in accordance with various aspects of the present disclosure. As can be appreciated, the drip chamber 500 may include elements that are similar to drip chamber 400. Therefore, similar elements may be referred to by similar reference numerals.

In the depicted example, the valve body 510 and knob assembly 530 can be disposed at an upper end of the chamber body 502. Therefore, medical fluid can enter the chamber body 502 through the valve body 510 and can exit the chamber body 502 through a chamber outlet 505. As can be appreciated, the valve body 510 can control the flow rate of medical fluid through the chamber body 502.

In some embodiments, the valve body 510 and the knob assembly 530 are coupled to the upper portion of the chamber body 502 at the receiver or chamber body coupling 512 defined within the knob assembly 530. As can be appreciated, medical fluid enters the knob assembly 530 through the valve inlet 514 and exits into the chamber body 502 through the valve outlet 520. Advantageously, the valve body 510 and the knob assembly 530 cooperatively control the flow of fluid from the valve inlet 514 to the valve outlet 520 and into the chamber body 502.

In some embodiments, a needle valve assembly can be formed between the valve body 510 and a knob assembly 530. Optionally, a needle valve inlet 515 can direct fluid flow from the valve inlet 514 into the needle valve assembly formed between the valve body 510 and the knob assembly 530. Therefore, during operation, the valve body 510 and the knob assembly 530 can control the flow between the valve inlet 514 and the valve outlet 520. In the illustrated embodiment, the valve body 510 can define a fixed needle valve surface 516. The fixed needle valve surface 516 can receive the movable needle valve surface 536 of the knob assembly 530. By axially moving the knob assembly 530, the cross-sectional area of the flow path defined between the fixed needle valve surface 516 and the movable needle valve surface 536 can be adjusted to control the flow rate between the valve inlet 514 and the valve outlet 520. Accordingly, during operation, fluid flow can enter the valve inlet 514, through the needle valve inlet 515, flow through the flow path defined between the fixed needle valve surface 516 and the movable needle valve surface 536 and exit into the chamber body 502 through the valve outlet 520.

As can be appreciated, the knob assembly 530 can be moved relative to the valve body 510 to adjust the flow rate between the valve inlet 514 and the valve outlet 520. In some embodiments, the knob assembly 530 can be in threaded engagement with the valve body 510 to allow for fine adjustment of the flow rate for the drip chamber 500. Therefore, by rotating the knob 532, the movable needle valve surface 536 of the knob assembly 530 can move relative to the fixed needle valve surface 516 of the valve body 510. In some embodiments, a threaded portion 534 of the knob assembly 530 can be in threaded engagement with a threaded portion 518 of the valve body 510.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

In one aspect, the term "coupled" or the like may refer to being directly coupled. In another aspect, the term "coupled" or the like may refer to being indirectly coupled.

Terms such as "top," "bottom," "front," "rear" and the like if used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Various items may be arranged differently (e.g., arranged in a different order, or partitioned in a different way) all without departing from the scope of the subject technology.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A drip chamber comprising:

a chamber body defining a chamber volume, the chamber body comprising a spike, an inlet tube extending through the spike, and an air vent between the chamber volume and an environment; and a valve body coupled to the chamber body, the valve body comprising:

- a chamber body coupling to receive and couple to the chamber body, wherein the valve body is disposed as a chamber body outlet such that a fluid from the chamber volume can enter the valve body;
- a valve inlet;
- a valve outlet; and
- a needle valve assembly comprising:
  - a fixed needle valve surface, wherein the fixed needle valve surface is frustoconical, the valve inlet extends through the frustoconical fixed needle valve surface, and the valve outlet extends through the frustoconical fixed needle valve surface; and
  - a movable needle valve surface, wherein the movable needle valve surface is frustoconical, nested within the frustoconical fixed needle valve surface, and the movable needle valve surface is axially movable between a first position radially closer to the fixed needle valve surface and decreasing a cross-sectional area of a flow path defined by the frustoconical fixed needle valve surface and the frustoconical movable needle valve surface between the valve inlet and the valve outlet and a second position radially spaced apart from the fixed needle valve surface and increasing the cross-sectional area of the flow path between the valve inlet and the valve outlet to control a flow rate between the valve inlet and the valve outlet wherein the valve inlet is disposed between an end of the movable needle valve surface and the valve outlet when the movable needle valve surface is in the first position.

2. The drip chamber of claim 1, wherein the spike defines a spike flow path in fluid communication with the chamber volume.

3. The drip chamber of claim 1, wherein the valve inlet is in fluid communication with the chamber volume.

4. The drip chamber of claim 1, further comprising a movable knob, wherein actuating the knob actuates the movable needle valve surface to control the flow rate between the valve inlet and the valve outlet.

5. The drip chamber of claim 4, wherein the movable knob is in threaded engagement with the valve body and rotating the knob actuates the movable needle valve surface to control the flow rate between the valve inlet and the valve outlet.

6. The drip chamber of claim 4, wherein the movable knob is axially movable relative to the valve body and axially moving the knob actuates the movable needle valve surface to control the flow rate between the valve inlet and the valve outlet.

7. The drip chamber of claim 4, wherein the movable knob defines the movable needle valve surface.

8. The drip chamber of claim 4, wherein the end of the movable needle valve surface is opposite the movable knob.

9. The drip chamber of claim 4, wherein the valve inlet is disposed radially between the end of the movable needle valve surface and the valve outlet.

10. A method to control fluid flow through a drip chamber, the method comprising:

providing a chamber body defining a chamber volume, a spike, and an inlet tube, the chamber body comprising an air vent between the chamber volume and an environment, and the chamber volume configured to receive the fluid flow from the inlet tube; and providing a valve body coupled to the chamber body via a chamber body coupling of the valve body, wherein the valve body is disposed as a chamber body outlet such that a fluid from the chamber volume can enter a valve inlet of the valve body;

wherein the valve body comprises a frustoconical movable needle valve surface movable between a first position radially closer to a frustoconical fixed needle valve surface and decreasing a cross-sectional area of a flow path defined by the frustoconical fixed needle valve surface and the frustoconical movable needle valve surface between the valve inlet and a valve outlet both extending through the frustoconical fixed needle valve surface, and a second position radially spaced apart from the fixed needle valve surface and increasing the cross-sectional area of the flow path between the valve inlet and the valve outlet, wherein the frustoconical movable needle valve surface is nested within the frustoconical fixed needle valve surface and the fluid flow passes through the valve inlet and the valve outlet both extending through the frustoconical fixed needle valve surface, wherein the frustoconical movable needle valve surface is movable between the first position and the second position to control the fluid flow out of the valve body, wherein the valve inlet is disposed between an end of the movable needle valve surface and the valve outlet when the movable needle valve surface is in the first position.

11. The method of claim 10, further comprising:

rotating a knob to move the movable needle valve surface relative to the fixed needle valve surface.

12. The method of claim 10, further comprising:

axially moving a knob to move the movable needle valve surface relative to the fixed needle valve surface.

13. The method of claim 10, further comprising:

providing a knob configured to be rotated to move the movable needle valve surface relative to the fixed needle valve surface.

14. The method of claim 13, wherein the end of the movable needle valve surface is opposite the knob.

15. The method of claim 10, further comprising:

providing a knob configured to be axially moved to move the movable needle valve surface relative to the fixed needle valve surface.

16. The method of claim 15, wherein the end of the movable needle valve surface is opposite the knob.

* * * * *